US008927258B2

(12) United States Patent
Galiano et al.

(10) Patent No.: US 8,927,258 B2
(45) Date of Patent: Jan. 6, 2015

(54) DEVICE AND METHOD FOR DIAGNOSTIC ANALYSES

(75) Inventors: Paolo Galiano, Padua (IT); Gian Piero Spezzotti, Udine (IT)

(73) Assignee: Alifax Holding SpA, Polverara (IT)

( * ) Notice: Subject to any disclaimer, the term of this patent is extended or adjusted under 35 U.S.C. 154(b) by 118 days.

(21) Appl. No.: 13/203,187

(22) PCT Filed: Feb. 24, 2010

(86) PCT No.: PCT/IB2010/000364
§ 371 (c)(1),
(2), (4) Date: Aug. 24, 2011

(87) PCT Pub. No.: WO2010/097683
PCT Pub. Date: Sep. 2, 2010

(65) Prior Publication Data
US 2011/0306032 A1  Dec. 15, 2011

(30) Foreign Application Priority Data

Feb. 25, 2009 (IT) .............................. UD2009A0046

(51) Int. Cl.
| C12M 1/34 | (2006.01) |
| C12M 3/00 | (2006.01) |
| C12M 1/36 | (2006.01) |
| C12M 1/38 | (2006.01) |
| C12Q 1/00 | (2006.01) |
| C12Q 1/04 | (2006.01) |
| G01N 35/02 | (2006.01) |
| G01N 35/10 | (2006.01) |

(52) U.S. Cl.
CPC ............ *G01N 35/028* (2013.01); *G01N 35/109* (2013.01)
USPC .................. 435/287.1; 435/286.2; 435/286.3; 435/286.4; 435/4; 435/34

(58) Field of Classification Search
CPC combination set(s) only.
See application file for complete search history.

(56) References Cited

U.S. PATENT DOCUMENTS

| 5,012,119 A | 4/1991 | Rhiner |
| 6,617,146 B1 * | 9/2003 | Naccarato et al. ............ 435/243 |
| 2007/0202564 A1 * | 8/2007 | Glasson et al. ................ 435/30 |
| 2007/0269853 A1 * | 11/2007 | Galiano ......................... 435/39 |

FOREIGN PATENT DOCUMENTS

WO    2006/021519    3/2006

OTHER PUBLICATIONS

Barnes et al., "Clinical Evaluation of Automated Antibiotic Susceptibility Testing with the MS-2 System," Journal of Clinical Microbiology, 1980, vol. 12, No. 4, pp. 527-532.
Rolinson et al., "New Method for Antibiotic Susceptibility Testing," Antimicrobial Agents and Chemotherapy, 1972, vol. 2, No. 2, pp. 51-56.

* cited by examiner

*Primary Examiner* — Chris R Tate
*Assistant Examiner* — Douglas F White
(74) *Attorney, Agent, or Firm* — Hamre, Schumann, Mueller & Larson, P.C.

(57) ABSTRACT

An integrated device for diagnostic analyzes used to verify the presence of bacteria in at least a biological sample mixed with a eugonic culture medium in liquid form, to classify at least the type of bacteria, and to test a series of antibiotics, selected from a group of characteristic antibiotics at least for the type of bacteria identified, identifying those effective to determine the antibiotic therapy. The device comprises, inside an integrated structure, first containing means provided with containing elements in which the biological samples to be analyzed are distributed, second containing means comprising recipients or micro-plates thermostated with wells containing a eugonic culture medium in liquid form in which a first fraction of the biological samples to be analyzed is dispensed, and a first recipient and second recipients or plates with a relative first well and second wells in which a further fraction of the biological samples which resulted positive to the analysis is dispensed.

32 Claims, 8 Drawing Sheets

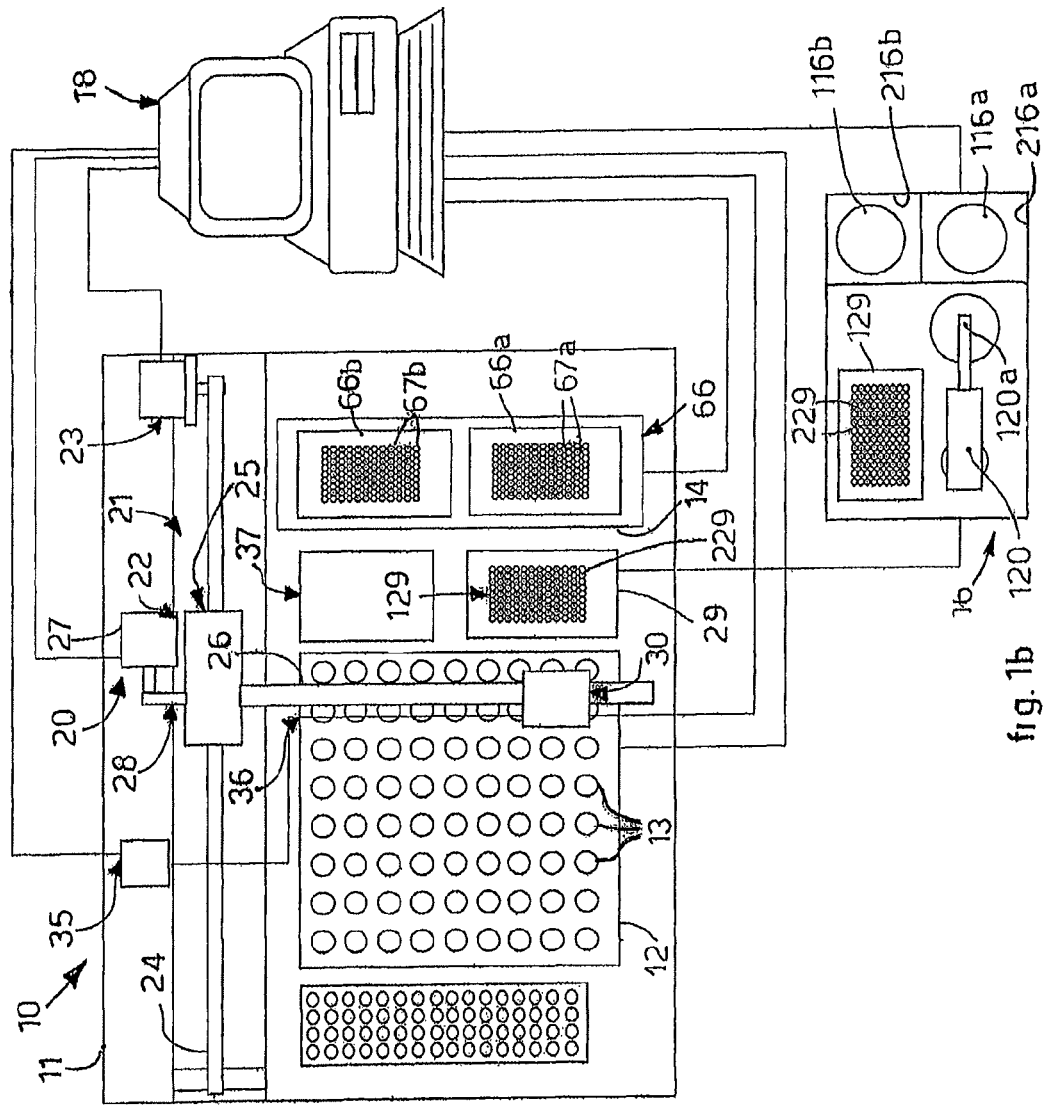

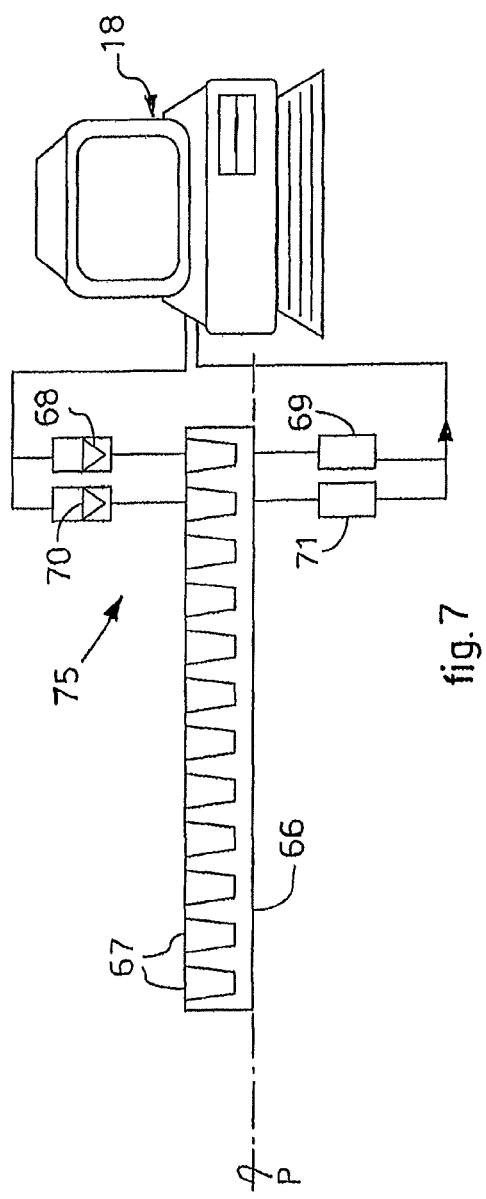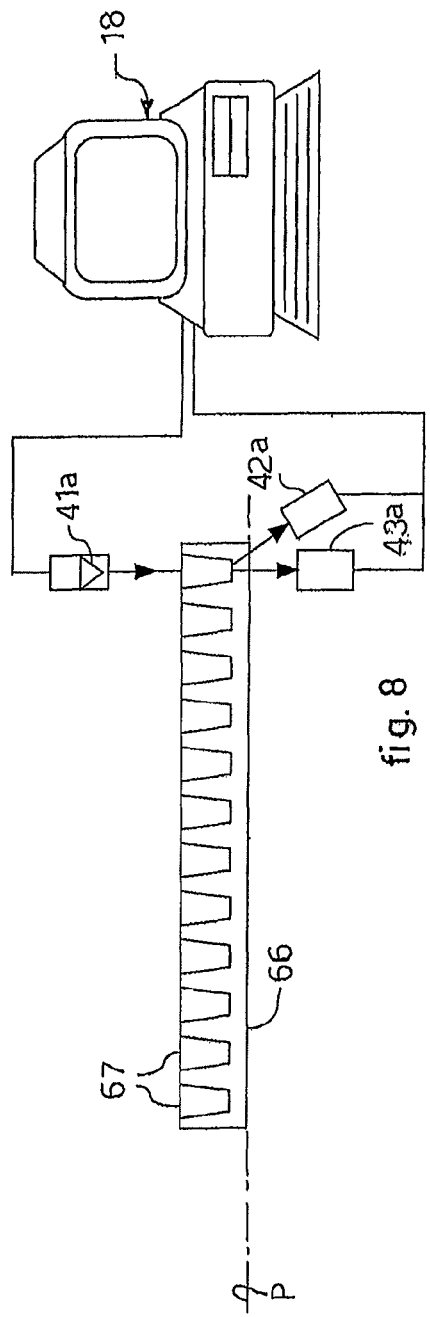

DEVICE AND METHOD FOR DIAGNOSTIC ANALYSES

FIELD OF THE INVENTION

The present invention concerns an integrated device, and a relative method to carry out diagnostic analyses on a biological sample, native or taken from the patient. The invention is used to verify the presence of one or more bacteria in the sample, to classify them or identify their type in order to choose the correct antibiotics used for possible therapy, which will subsequently be analyzed together with the bacterium identified, so as to verify their effectiveness and to supply an automatic flow of the bacteriological analyses without any manual intervention of an operator, starting from the taking of the sample from the urine container, test tube, various container or other.

The biological sample to be analyzed, or primary biological sample, can be for example urine, or other sterile or non sterile human biological fluid.

BACKGROUND OF THE INVENTION

In the field of diagnostic analyses various techniques are known to verify the presence of pathogenic organisms and micro-organisms in a biological sample, to classify and/or identify the type and to identify a group of antibiotics able to stop their proliferation in various parts of the human body. This latter operation is technically called antibiogram.

Known techniques to carry out the antibiogram provide to verify the functionality of the antibiotics in suspensions of isolated bacteria and therefore presuppose preventive and long isolation methods, to which the time required for the subsequent verification of the functionality of the antibiotics must also be added. The known methods of bacteria identification provide analysis techniques of the biochemical type always starting from isolated colonies.

The time needed to carry out culture tests (evaluation of bacterial growth), to identify and carry out the antibiogram is long, particularly for serious infections, and this can be dangerous for the patient. It is therefore common for physicians to administer in advance to the patient, without the support of diagnostic tests and exclusively according to a clinical suspicion, a broad-spectrum antibiotic to allow the therapy to be started immediately. The indiscriminate use of such antibiotics induces the so-called phenomenon of drug resistance. One disadvantage deriving from the use of such broad-spectrum antibiotics consists, for example, of the fact that, although such drugs are initially effective against bacterial growth, it may happen that not only are they not able to completely eradicate all the bacterial colonies, but even the surviving bacteria become resistant to the antibiotic chosen by means of genetic mutation and subsequently they proliferate, thus increasing the infection.

The scientific publication by Barnes et al., in the Journal of Clinical Microbiology Vol. 12, No. 4, October 1980 entitled "Clinical Evaluation of Automated Antibiotic Susceptibility Testing with the MS-2 System" is known: it describes an automated antibiotic susceptibility analysis starting from bacteria preliminarily isolated in Petri dishes, or discs. However, obtaining isolated bacteria provides that the sowing has already been carried out, manually or automatically. Moreover Barnes et al. provides a manual visual adjustment by the operator of the desired McFarland turbidity value and uses pre-selected cartridges to carry out the antibiogram.

A solution to the above mentioned disadvantages was proposed in the patent application WO-A-2006/021519 in the name of the present Applicant. This solution, although it is extremely effective in that it allows to obtain an indication of positivity of a sample and the selection of an effective family of antibiotics in a short time, has shown that it can be improved in terms of recognizing and isolating the type of germs or bacterium present in the positive sample.

In particular, purpose of the present invention is to offer a type of complete and automated bacteriological examination, particularly to perform the bacterial growth and the antibiogram, which allows on the one hand to obtain a quick and sufficiently reliable result and on the other hand to have a confirmation of the results with traditional methods, in a completely automated way, that is, reducing to a minimum the intervention of the operator, with obvious operating advantages starting with the taking of the initial sample.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purpose, a device according to the present invention comprises first containing means (primary sample zone) containing a plurality of test tubes or similar containers in which the biological samples to be analyzed are distributed, and second containing means (growth and reading zone) in which at least a first fraction of the primary sample is disposed. According to the present invention, the second containing means provide a plurality of recipients such as phials, test tubes, or the like, or micro-wells, containing a liquid culture ground, or eugonic culture medium, able to promote bacterial growth for the analysis.

The first and the second containing means are also disposed in a substantially integrated structure.

Furthermore each of the first and second containing means has a specific function in a specific phase of the method.

The integrated device according to the present invention also comprises, advantageously in the same integrated structure, third containing means, containing solid culture means, in which it is possible to automatically sow and plate a portion, or second fraction of the primary biological sample, for example on a typical Petri dish.

The device according to the present invention also comprises first examining means able to verify the presence of bacteria in said biological samples contained in the test tubes of the second containing means, so as to detect corresponding positive biological samples and possibly to classify or identify at least the type of bacteria present in said positive biological samples, in order to select a group of antibiotics appropriate to these.

The antibiotics of the group are selected as desired, or they are selected because they have already been administered to the patient by the ward, to give a suitability reply to the therapy started.

The integrated device according to the present invention is also provided with second examining means able to verify, on recipients or micro-wells of the second containing means in which a third fraction of the samples which have turned out positive is disposed, the sensitive or resistant response of each positive biological sample to a series of antibiotics of the group of antibiotics programmed or possibly selected by said first examining means.

According to one feature of the present invention, the second fraction of the biological sample corresponding to a sample found positive by said first examining means is taken from the first containing means and disposed, inoculated or sown, in the third containing means, to carry out a traditional analysis on solid culture ground, for example on a Petri dish, by which the said bacteria are isolated and/or identified, to confirm or not the result of the analysis of the quick culture test carried out on the second containing means in a eugonic medium.

An advantageous solution of the present invention also provides, preferably in the same integrated structure, fourth containing means ("parking" zone for primary samples on a micro-plate), for example a micro-plate placed in a cooled unit, to preserve at least part of the primary biological sample in a stable refrigerated condition.

Therefore, according to an advantageous solution, the primary sample or part of it is deposited and preserved in the fourth containing means, a part of the primary sample which has been recognized as positive is taken from the fourth containing means and this part is sown and plated in the third containing means.

According to an advantageous feature of the present invention, at least part of the primary biological sample is taken from the first containing means and disposed in the fourth containing means, in order to preserve it, advantageously on a refrigerated plate, in view of a possible plating in the third containing means, if the primary sample turns out positive in the analysis of the quick growth test.

Consequently, when it is necessary, said second fraction of the biological sample corresponding to a sample found positive by said first examining means is advantageously taken from the fourth containing means to be sown in the third containing means, so as to obtain the isolation and/or identification of said bacteria, advantageously on a Petri dish or the like.

The device also comprises, a movement and selection unit governed by a control unit to automatically pick up at least the positive biological samples and dispense them at least in the second and third containing means.

In a further variant, the second containing means comprise a heating unit associated with the first and the second analysis zone. This heating unit, together with the function performed by the eugonic medium and possibly with the continuous stirring of the growth medium by means of a magnetic bar placed on the bottom of the container, promotes and accelerates the bacterial growth of the positive biological samples.

In another variant, the second containing means comprise at least a micro-plate containing micro-wells in which the biological sample and the eugonic medium will be dispensed.

The control unit according to the invention is able to control and command all the sampling steps, the first dispensing of the samples in the liquid culture broths and the second dispensing of all the samples to carry out the "stand-by" parking in the refrigerated micro-plate of the fourth containing means.

The complete automation which is obtained with the present invention, in which there is substantially no intervention by the operator, surpasses the partial automation of automated platers which, although sowing the sample to be analyzed on Petri dishes, do not proceed to further automated steps in that, after the initial partial automation, there is no automatic dispensing in further containers of the culture mediums corresponding to the samples which are positive to bacterial growth in order to test the positive sample with a series of antibiotics to carry out the clinical antibiogram step.

A method for diagnostic analysis comes within the scope of the present invention, used to verify the presence of bacteria in at least a biological sample mixed with a eugonic culture medium, to verify the presence of bacteria and possibly to identify or classify at least the type of bacteria, and to test a series of antibiotics, selected from a group of characteristic antibiotics or already administered to the patient by the ward, pre-selected or oriented by the type of bacteria identified, identifying those effective to determine the antibiotic therapy.

According to the present invention, the method provides a first examining step or culture step, advantageously in a liquid culture ground or eugonic medium, during which a first fraction of the content of a plurality of biological samples is examined to verify the presence or not of bacteria in the sample, so as to define a plurality of positive biological samples, and in the case of positivity to determine the bacterial count thereof, and possibly to identify or classify the type of bacteria so as to program a series of antibiotics to actuate the clinical antibiogram, that is, the antibiogram without knowing the type of bacteria isolated and identified in the sample or the antibiogram toward the drug, whose germicide function is to be tested, administered by the ward doctor In a non-restrictive embodiment of the invention, the count of the organisms present in the sample is determined on the basis of kinetic calculations performed on the curve of the bacterial growth obtained.

With the present invention it is possible to signal, by means of a monitor display or acoustic signaling, the possible turbidity detected by the first examining means in the second containing means corresponding to the signal of bacterial growth present in the sample being tested, when the 0.5 McFarland turbidity value is reached calculated on the basis of the growth dynamics detected.

Furthermore one can also possibly use, in the appropriate instrument, a standard turbidity control latex, so as to be able to verify the 0.5 McFarland turbidity and subsequently carry out the suitable antibiogram.

It is thus possible to perform the antibiogram directly, using as an inoculums the same eugonic medium ready at the 0.5 McFarland turbidity level requested. Moreover, advantageously, at the same time as the 0.5 McFarland turbidity level is reached, with a measurement correlated to the international turbidity standards, the present invention, with an acoustic alarm, alerts the operator so that he can accede in the shortest time possible to the subsequent investigations, typically the antibiogram.

Other methods and/or other reference parameters are however possible within the scope of the present invention.

According to an advantageous feature of the present invention, during the course of the second step a passage is provided, for example at the same time as the first step, in which each of the primary biological samples, or a fraction of each of the biological samples, is replaced in a refrigerated micro-plate in a refrigerated block (storage zone for refrigerated micro-plates, fourth containing means).

According to the present invention, in a second examining step, in the case of positivity of the native sample to the quick growth of the first step, a part of the same is taken, from the fourth containing means, by means of a suitable movement element of the movement unit, such as a calibrated loop-shaped tube, and swiped automatically on a solid culture ground, such as a Petri dish, to obtain the isolation and/or identification of said bacteria, in particular in the third containing means for sowing in the culture ground, in order to confirm the rapid analysis of the first step.

The culture ground, in a preferential solution of the invention, is a solid means such as for example that typically used on Petri dishes.

The sowing process in a solid culture ground, limited to only samples resulting positive to quick growth (growth in a eugonic medium), automatically allows to dispense the native sample, to obtain the isolation of the bacteria.

According to a variant of the invention, following this isolation, one proceeds with the classic method which provides to prepare a 0.5 McFarland suspension obtained by diluting the isolated colonies in a saline physiological suspension.

As we said, the first examining or analysis step, that is, the quick culture of the sample in liquid medium which can last from 45 minutes to 3 hours, allows to obtain positive samples and for each of these to determine whether the 0.5 McFarland turbidity value has been reached, obtained during the exponential growth step, and to discard all the negative samples.

The culture medium of the samples detected positive will be used directly as inoculums for the so called "clinical" test of the antibiogram, thus named because it does not provide the prior isolation and identification of the bacterium (Cummitech 2b 1998).

In this way, on samples marked with McFarland equal to 0.5, the antibiotics normally used by clinics as first antibiotic therapy can quickly be tested without passing through the step of identifying the bacterium present. This clinical or preventive antibiogram method can be useful in quickly monitoring the functionality of the drug for commonly used antibiotics or to intervene effectively or promptly on patients in intensive care and therefore at risk of their lives, given that a rapid verification of the functionality of the antibiotic toward the specific bacterium being tested can allow to optimize the treatment quickly and therefore to overcome the patient's critical step (Rello J et al. Am J Respir Crit Care 1997; 156:196-200 Kollef M H et al. Chest 1998; 113:412-420 Chastre J et al. Am J Respir Crit Care 2002; 295:867-903 Chastre R Resp. Care 2005; 50 (7); 975-983 Tamura K Clin Infect Dis 2004, 39 (suppl 1): S59-64).

To this purpose, the method according to the present invention provides a third examining step, during which, on a third fraction deriving from the culture medium corresponding to the biological sample positive to quick growth in the first step, the sensitive or resistant response of each biological sample positive to a series of antibiotics selected in said first examining step is verified.

In other words, for only those samples which have proved positive to the quick bacteria growth test (in liquid medium), the sowing of the native sample is further carried out, taken from the suitable module (refrigerated micro-plate) of the third containing means, typically on Petri dishes, so as to allow the isolation and exact identification of the germ with, the traditional method, thus allowing to refine and complete the therapy plan.

The analysis according to the present invention is completely automated and substantially does not require the intervention of an operator during the entire execution. The analysis provides rapid results on the basis of the sensitive or resistant response of the bacterium to the series of antibiotics tested (clinical antibiogram).

According to a variant of the present invention, the first containing means comprise a cooling unit, for example a refrigerated block, with the function of maintaining unaltered the characteristics of the biological samples taken from the patient, preventing the relative bacterial load from modifying.

In a variant, the first and the second examining means comprise electromagnetic radiation emitters, for example coherent light, and means to detect said electromagnetic radiations. Preferably, the emitter means and the detection means are disposed substantially on a circumference, in the center of which, depending on the examining step in progress, we will find the recipient containing the biological sample to be classified or the recipient containing the biological sample already classified as type of bacterium and which is to be subjected to the antibiogram.

In a further variant, it is provided to associate with the micro-wells of the micro-plates a light scattering reading system, in which the electromagnetic radiation emitters, for example of coherent light, are positioned vertically above the micro-plate and the detection means are disposed vertically under the micro-wells.

The first and the second examining means detect growth curves of the microorganisms depending on the time and, on the basis of the curves detected, the control unit verifies the presence of bacteria, and can classify them on the basis of some analytical parameters extrapolated from the growth curves. In this way functionality tests can be carried out in vitro for antibiotics suitable for the therapy. The growth curves also describe the morphology of the bacterium.

According to a variant, a verification step or control examination is provided, in order to evaluate the correctness of the examination carried out by means of isolating the bacteria obtained by dispensing the sample on the Petri dishes.

The present invention overcomes the disadvantages and the limitations of the state of the art, automatically carrying out the antibiogram directly from the sample in the execution step and not from the isolated bacteria. The passage to the antibiogram step occurs, with the present invention, not from the isolated bacterium, but from the exponential growth step using a mathematical algorithm of detection of the bacterial growth expressed in CFU.

There is an automatic sequential antibiogram step, without passing through the identification of the bacterium by means of the traditional Petri dish or selective discs, where, normally, the sample would be inoculated in order to isolate the bacteria.

Moreover, the automatic way in which the 0.5 McFarland turbidity is reached and signaled overcomes the operating limits of the state of the art.

Furthermore, the invention carries out the autobiogram test in liquid form, directly from the sample to be analyzed during the exponential growth step, as soon as the conditions detected of McFarland turbidity, or counts in CFU by means of the growth and calculus algorithm, are automatically detected, thus avoiding the bacteria isolation method.

Furthermore, compared with the state of the art, the invention allows to carry out the sowing of only the samples showing positive in the automation step, thanks to the automatic detection of the McFarland turbidity.

The invention therefore provides an automatic analysis, without any handling of the sample, having a sequential work flow that comprises bacterial growth, the attainment of the desired McFarland turbidity value, the antibiogram without identification and the automatic plating of the positive samples for identification on Petri dishes or the like. The synergetic coupling of these operations or steps allows to make a completely automatic work flow, overcoming the problems and the limits of the state of the art.

BRIEF DESCRIPTION OF THE DRAWINGS

These and other characteristics of the present invention will become apparent from the following description of a preferential form of embodiment, given as a non-restrictive example with reference to the attached drawings wherein:

FIGS. 1, 1a and 1b schematically show forms of embodiment of an integrated device for diagnostic analyses according to the present invention;

FIG. 7 shows a variant of the device in FIG. 1;

FIG. 8 shows another variant of the device in FIG. 1.

DETAILED DESCRIPTION OF A PREFERENTIAL FORM OF EMBODIMENT

Figure 1:
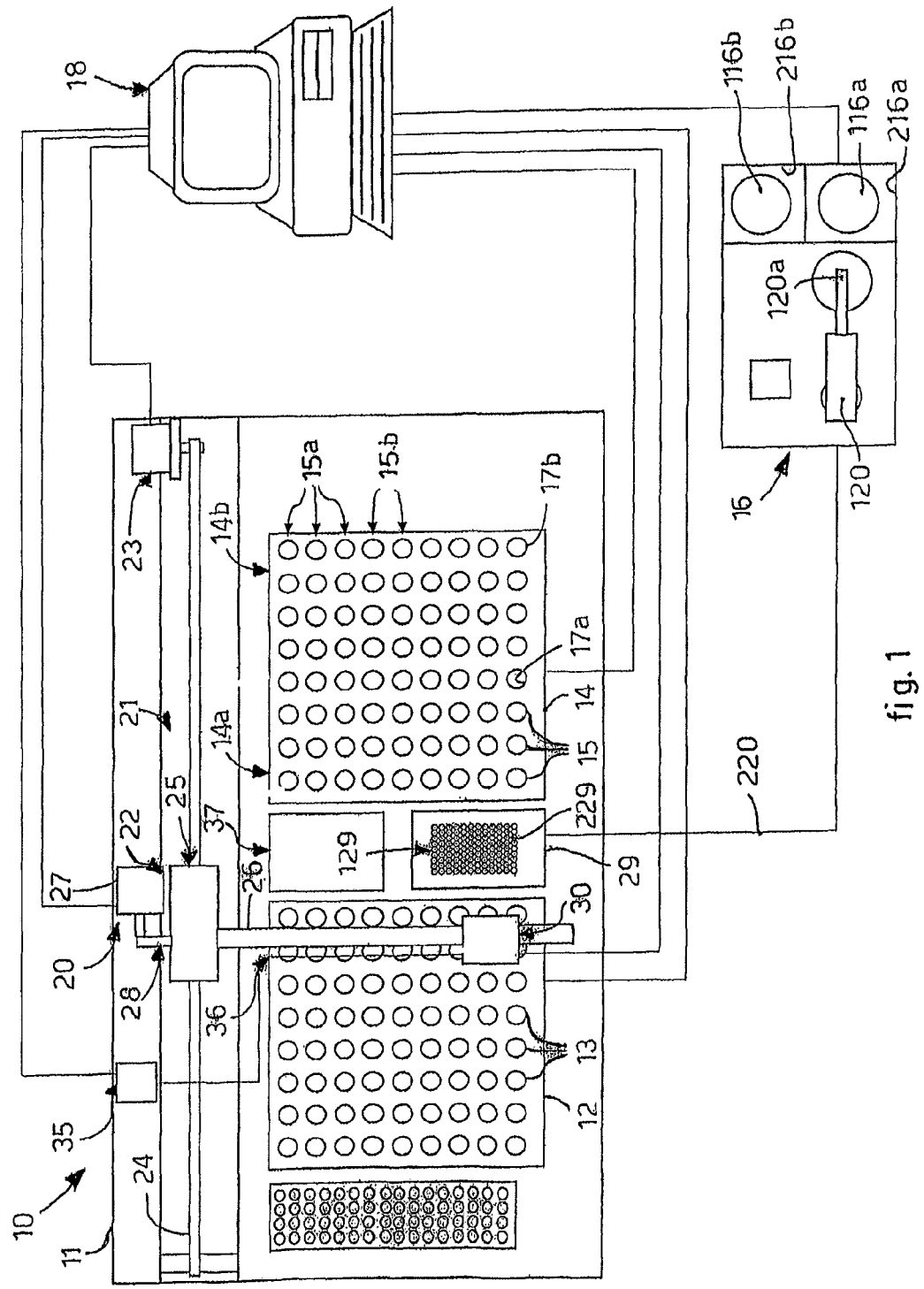

With reference to FIG. 1, an integrated device 10 for diagnostic analyses according to the present invention comprises, in an integrated structure 11, a first container 12 containing a plurality of test tubes 13, inside each of which a pure biological sample is present, for example urine, or other human biological liquids, sterile or non-sterile.

The first container 12 is associated with a cooling unit, not shown, which brings or keeps the temperature of the biological samples within a range comprised between 2° and 8° C., to prevent the variation of the characteristics of the biological samples and to keep the bacterial load stable.

The device 10 also comprises a second container 14 which has a first analysis zone 14a containing a plurality of culture recipients or phials 15, disposed in relative seatings 17a, and a second analysis zone 14b.

The second container 14 is associated with a heating unit, not shown, to heat to a temperature comprised between about 35° C. and 37° C. the biological samples to be analyzed, so as to promote the bacterial growth of any bacteria present.

The device 10 further comprises a third container 16 provided with a refrigerated cupboard, not shown in the drawings, which comprises a plurality of seatings in which Petri dishes are housed. In particular the third container 16 provides a first refrigeration section 216a in which plates 116a are placed, which are kept refrigerated until used, while waiting to be sown, while in a second section 216b of the cupboard a thermostated part is provided in which Petri dishes 116b, which have already been sown, are incubated. The refrigerated plates 116a, after they have been inoculated with the sample taken from the fourth container, are placed in the second section 216b, and are represented or indicated, for convenience, with the reference number 116b.

In the device 10, an analysis module for the storing of all samples is also advantageously provided, so as to be able to carry out, only on the samples which have turned out positive to quick growth, the culture on solid ground (Petri dish) in the third container 16. The analysis module comprises a fourth container 29 containing at least a micro-plate 129 made up of empty micro-wells 229 in which the samples which have been subjected to the quick culture test are stored. In the micro-wells 229 a certain quantity is introduced of the same biological samples dispensed in the recipients 15 of the second container 14.

A control unit 18 is associated with the integrated device 10, for example to an electronic calculator, which can be either inside the integrated structure 11 or outside it.

The integrated device 10 also comprises, a movement and selection unit 20, controlled by the control unit 18, to automatically move a sample, or parts of it, at least from the first container 12 to the second container 14 and to the fourth container 29, and to move parts of the sample between the analysis zones 14a and 14b of the second container 14, as will be explained in more detail hereafter.

The movement and selection unit 20 consists of a guide 21 on which a movable support 22 moves linearly, moved by a first motor 23 by means of a first belt 24. The movable support 22 comprises a head 25, to which an arm 26 is constrained, associated with a second motor 27 able to move, by means of a second belt 28, a selection head 30 free to slide on the arm 26.

Figure 2:
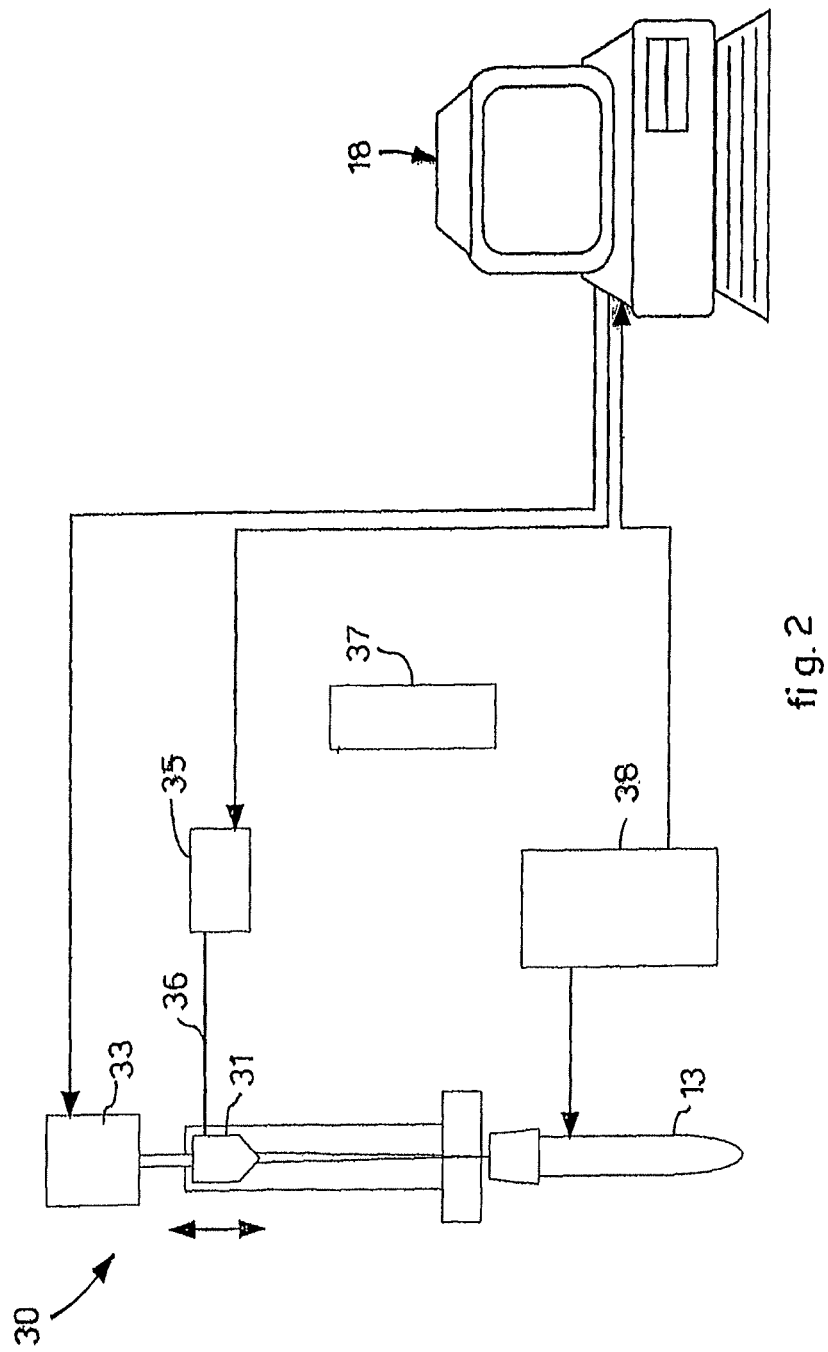
FIG. 2 schematically shows a detail of the device to take samples and identify the primary sample.

The selection head 30 (FIG. 2) comprises a sample taking and dispensing needle 31, and an actuator 33 able to selectively move the needle 31.

The selection head 30 is connected to a pumping mechanism 35 by means of a pipe 36, advantageously of the flexible type, for example made of rubber.

The control unit 18 drives the pumping mechanism 35 to take and distribute, by means of the needle 31, a desired quantity of the biological sample for the various dispensing steps.

The movement unit 20 also comprises a mechanic arm member 120 in correspondence to the third container 16, provided in this case with a calibrated loop-shaped tube 120a, by means of which the primary sample (positive), which was previously stored in the fourth container 29, is taken and dispensed in one of the plates 116a of the third container 16, or the sample placed in the fourth container 29 is sown in the third container 16.

In particular FIG. 1 indicates the variant in which the primary biological sample taken and moved hydraulically from the fourth container 29 by means of a connection, or hydraulic tube 220 and is carried to the arm member 120 and from here is put in the plate of the third container 16.

Figure 1A:
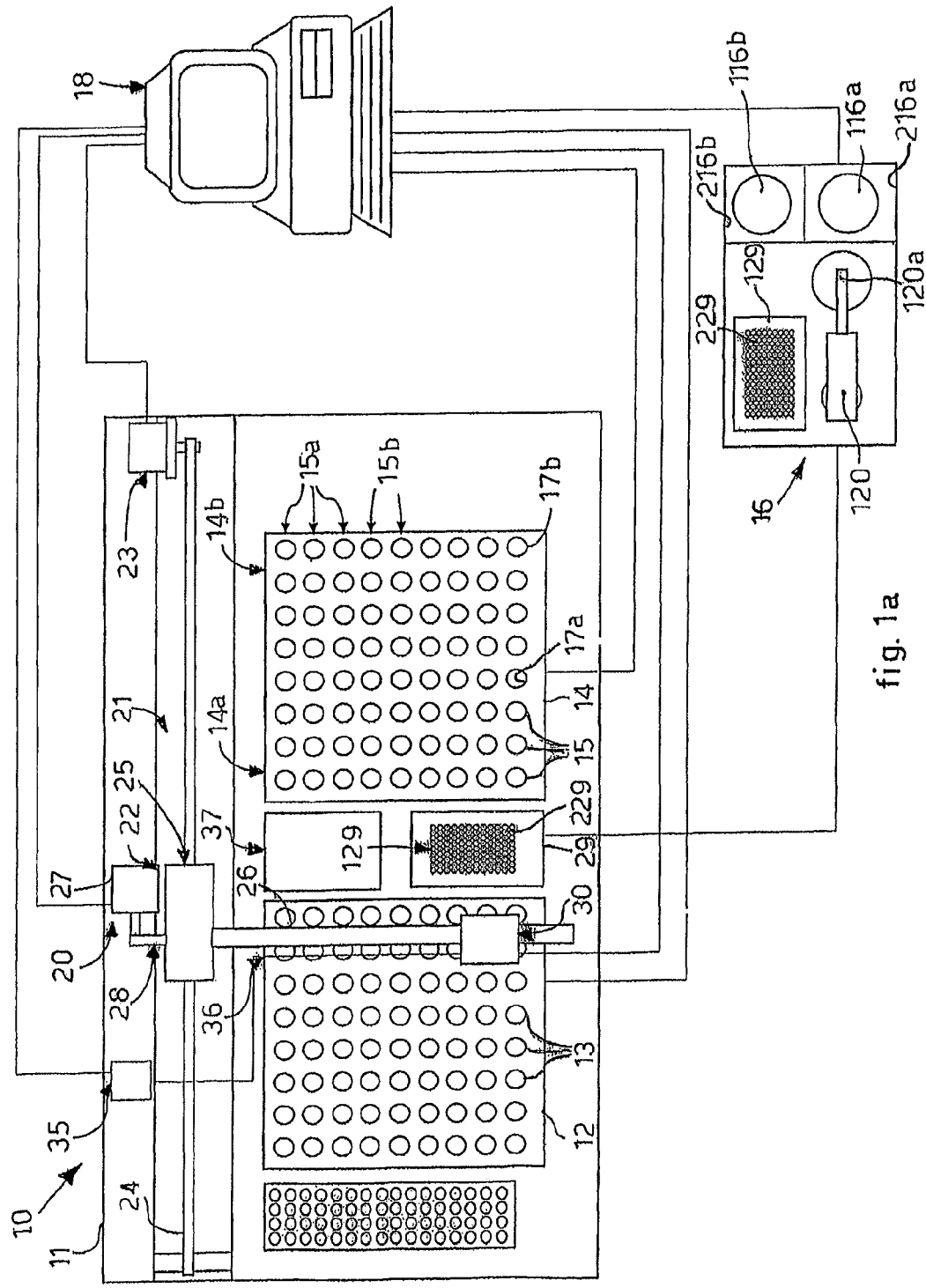

In FIGS. 1a and 1b a further solution is shown in which, by mechanical movement means, the plate 129 can be moved directly from the fourth container 29 and deposited in the third container 16, from where the mechanical arm member 120 takes the desired sample directly from one of the wells 229 and puts it in a plate 116a, which in its turn will be located in the second section 216b of the third container 16 (dish 116b).

Moreover, in FIG. 1b the variant is shown in which in the second analysis zone 14, micro-plates 66 are used instead of the recipients 15.

The integrated device 10 also comprises a washing zone 37, consisting for example of a tank, for the internal and external sterilization of the needle 31, which is advantageously carried out after each sampling and dispensing operation, in order to avoid every contamination of bacterial load between the different biological samples which have been sampled and dispensed.

Figure 3:
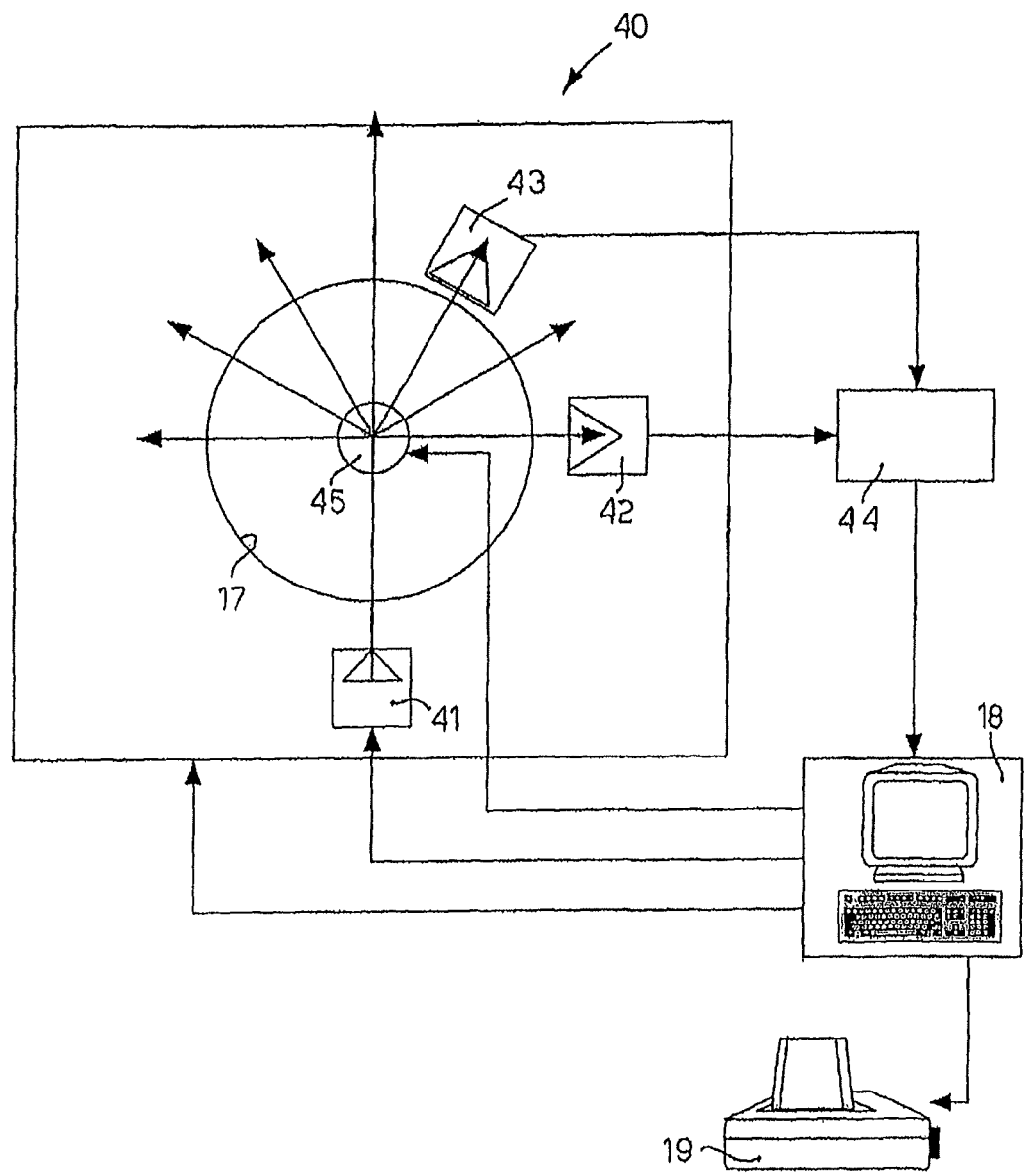
FIG. 3 schematically shows a further detail of the scattering reading device in FIG. 1.

The second container 14 comprises, advantageously for each seating 17a of the first analysis zone 14a, a first examining device 40 (FIG. 3), of a known type, having a laser emitter 41, with which a first sensor 42 and a second sensor 43 are associated, disposed respectively at about 90° and 150° with respect to the laser emitter 41 and able to detect the light which, emitted by the laser emitter 41, passes through the recipient 15.

The data gathered by the first sensor 42 and the second sensor 43 are sent to the control unit 18 by means of a conditioning device 44, which amplifies, filters and processes the data gathered.

The second container 14 comprises, as has been said, the first 14a and the second 14b analysis zones, the latter with relative seatings 17b in which to house recipients 15, in particular first recipients 15a, which, as will be seen hereafter, act as reference samples, and second recipients 15b. Advantageously, for each seating 17b of the second analysis zone 14b, the second container 14 comprises a second examining device 49 of the known type and similar to the first examining device 40.

Figure 5:
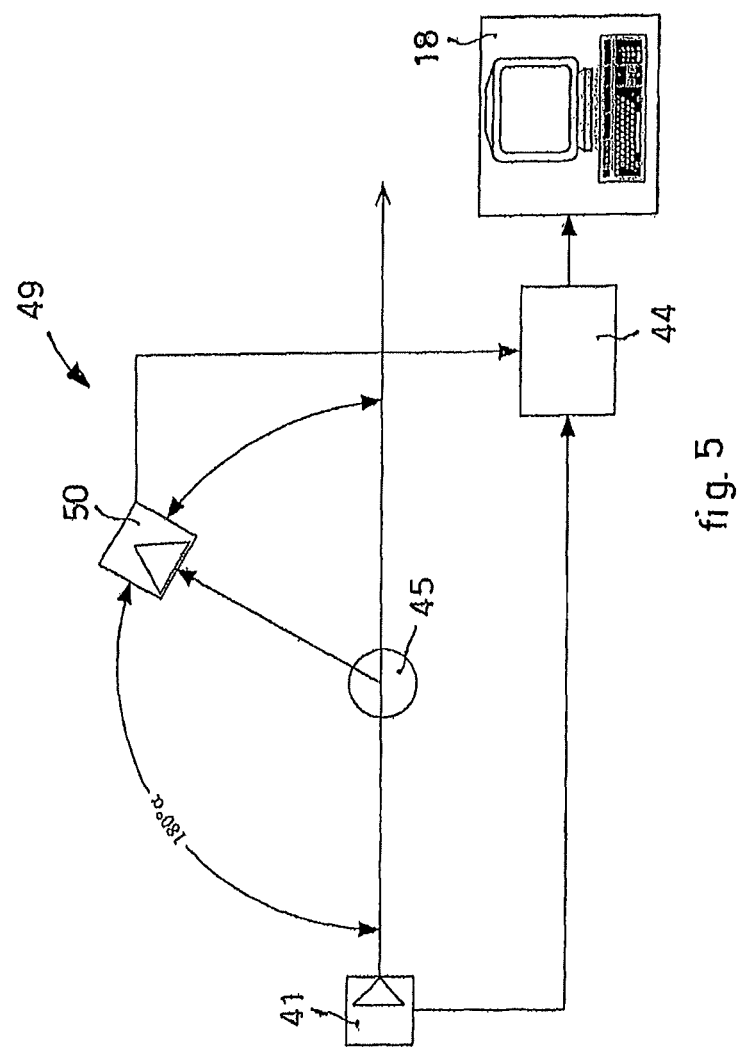
FIG. 5 schematically shows a variant of the scattering reading device with the movable detector on the semi-circumference.

In the solution in FIG. 5, the second examining device 49 comprises a laser emitter 41 with which a single sensor 50 is associated, movable on an arc of a circumference which subtends an angle of about 180° or a similar curved sensor which covers the same angle, and moved by a motor, driven by the control unit 18 and not shown in the drawings.

In this case too the data gathered by the sensor 50 is sent to the control unit 18 by means of the conditioning device 44.

Figure 4:
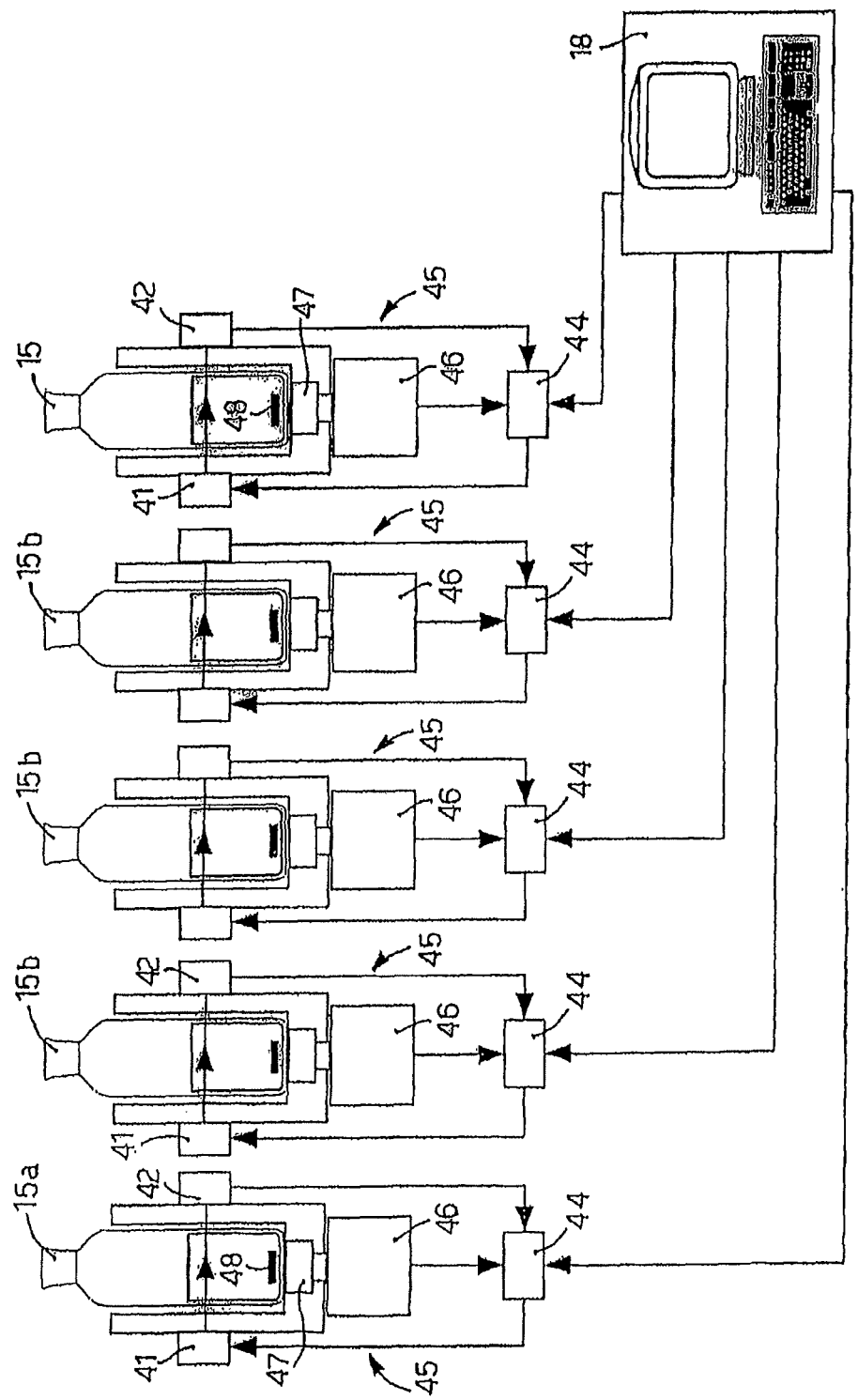
FIG. 4 schematically shows another detail of the mixing and reading device in FIG. 1.

Every first 40 and second 49 examining device also comprises a stirring unit 45 (FIG. 4), provided with a stirrer motor 46 controlled by the control unit 18, to put a first magnet 47 in rotation connected mechanically to the stirrer motor 46, and able in its turn to put in rotation a second magnet 48, inserted inside the corresponding recipient 15 so as to mix the contents of the latter.

In an alternative variant, instead of recipients 15, the second container 14 advantageously comprises several growth micro-plates 66 (FIGS. 1b, 7 and 8) containing micro-wells 67, properly thermostated and having been stirred. In particular in the solution shown in FIG. 8, there is a laser emitter 41a disposed on the opposite side, relative to the lying plane P of the plate 66, with respect to a first sensor 42a and second sensor 43a which is positioned vertically above the plate 66 and the wells 67.

The first sensor 42a and second sensor 43a will be located vertically under the wells 67, respectively at about 90° and 150° with respect to the lying plane P of the plate 66, to detect the light emitted by the laser emitter 41a which passes through the micro-well 67.

Figure 6:
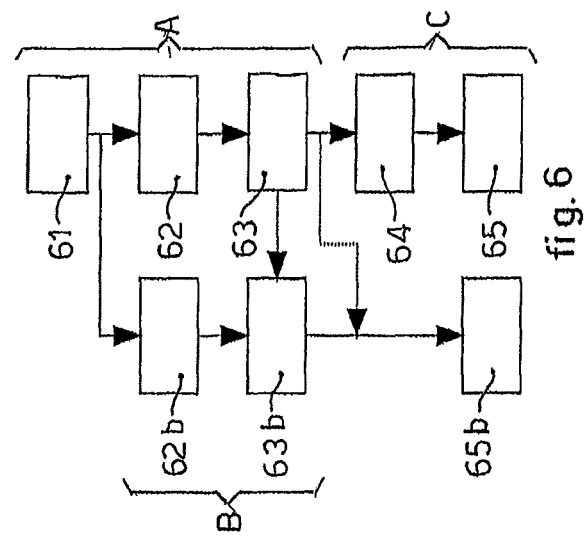
FIG. 6 shows a flow chart of a method for diagnostic analyses according to the present invention.

The integrated device 10 as described heretofore operates according to a method, indicated overall by 60 in FIG. 6, which provides, macroscopically, three examining steps, A, B and C, each of which comprises respective procedural sub-steps.

The first examining step A, in a first sampling sub-step 61, provides that the control unit 18 drives the movement and selection unit 20 to take a desired quantity, first fraction, of a specific biological sample from the respective test tube 13.

In a second dispensing sub-step 62 on the reading unit, the said first fraction, or a part of this quantity, is dispensed by means of the movement and selection unit 20 into a recipient 15 (FIGS. 1, 1a) or into a micro-well 67 (FIG. 1b) disposed in the first analysis zone 14a, sterilized and inside which there is a liquid culture ground or eugonic medium for the bacterial growth. The eugonic medium can already be present inside the recipient 15 or in the micro-well 67 before the biological sample is dispensed, or it can be inserted subsequently. In said recipient 15 or micro-well 67 the growth of bacteria which are possibly present occurs.

In parallel, the second examining step B provides a further dispensing sub-step 62b, by means of the movement and selection unit 20, of the primary biological sample and of a further fraction into a seating or micro-well 229 of the refrigerated plate 129 of said fourth container 29 (dispensing on buffer micro-plate), in order to conserve it in view of a possible confirmation examination on a Petri dish 116a, 116b.

When the sampling sub-step 61 and the dispensing sub-step 62 are finished, the first examining step A provides a detection and classification sub-step 63 during which the control unit 18 activates the first examining devices 40, so that the sensors 42, 43 of each device 40 periodically detect the laser emissions emitted by the laser emitter 41.

The biological samples, with the presence of duplicating bacteria, emit signals of diffused light which the control unit 18 processes to supply, starting from about 45 minutes from the beginning of incubation, specific curves which express the development of the bacterial growth over time.

From the signals provided by the two sensors 42 and 43, two growth curves of possible bacteria are obtained, having respective slopes and a reciprocal spread which allow to verify the presence of the bacterium and to classify its type (sub-step of bacteria detection and classification 63 by the reading unit).

The signal obtained from the second sensor 43 with an angle of 150° defines a first curve relating to the presence of bacteria and consequent measuring of the bacterial load over time.

Moreover, the signals obtained by the first sensor 42 with an angle of 90° are more characterized by the morphology of the bacteria and define a second curve of these.

The slope ratios and the differentiations between the two curves allow to identify or classify the bacteria possibly present.

Then, the control unit 18 selects the bacteria belonging to the coccus type, which have a characteristic spread of the growth curves which enables it to be distinguished from the *bacillus* type.

Having determined which the positive biological samples are, in the second examining step B the control unit 18 controls the sample taking, from the seatings or micro-wells 229 of the fourth container 29 (refrigerated micro-plate), of the fractions preserved and corresponding to samples detected positive and, by means of said movement and selection unit 20, in particular as shown previously for FIGS. 1, 1a and 1b, takes only the samples corresponding to those which were found positive and inoculates them, dispensing and growth sub-step 63b of only positive samples, in the dishes 116b of the third container 16, containing a solid culture ground, for example Petri dishes or similar, to confirm the quick growth test.

Thanks to this dispensing and growth sub-step 63b of only those samples shown positive on the dishes 116b, the separation of the single colonies on solid ground can be obtained, in order to obtain further information of the type of bacterium or germ present in the original sample.

In a preferential solution, in the Petri dishes 116a, 116b solid grounds of the chromogenic type are used, thanks to which a presumptive diagnosis of the specific bacterium or micro-organism present in the original sample is obtained.

In another solution, using the bacterial colonies isolated in said Petri dishes 116a, 116b, the execution is provided of biochemical-type tests to identify the bacteria in the traditional method.

Therefore with the first examining device 40 the control unit 18 verifies the presence of bacteria in a corresponding recipient 15 and, if positive, identifies the type by analyzing the ratio between the signals obtained by the second sensor 43 and by the first sensor 42, and also, in parallel, proceeds to plate them in the Petri dishes 116a which are then incubated (Petri dishes 116b), to verify the quick analysis test.

The sensitivity count thresholds of the bacterial growth start from about 1 unit (Colony Forming Unit cfu/ml), that is, the number of units forming colonies per millimeter of biological sample, up to about 100 million cfu/ml. The integrated device 10 is therefore able to carry out a diagnostic analysis with a variable sensitivity range, also according to the type of sample, whether sterile or from an intermediate section.

The control unit 18 is connected to an output device 19 (FIG. 3), in this case a printer, or an external memorization device, not shown, such as for example hard disk, floppy disk, CD-ROM, DVD-ROM, flash-memory, USB mass storage device, solid state memory or the like, respectively for printing and memorizing at least the data concerning the curves given by the control unit 18. The latter also memorizes the curves per type of growth with respect to the bacteria identified, so as to provide a database for comparison for each type of examination carried out.

Moreover, in the third examining step C, the control unit 18, by means of the first examining device 40, verifies the suitability of the positive biological samples for the execution of the clinical antibiogram, evaluating the necessary turbidity (equivalent to 0.5 McFarland) or signaling the possible non-suitability for this examination by means of the output device 18 and/or by means of an acoustic signaler.

In particular in said third examining step C, when the detection and classification sub-step 63 is finished, a second sub-step of sample taking and dispensing 64 follows, during which the control unit 18 drives the movement and selection unit 20 to take the positive biological samples enriched by the presence of grown bacteria, recognized as such during the previous sub-step 63, to dispense them in a group of first 15a and second 15b recipients, located in the second analysis zone 14b, which make up the panel for the antibiogram.

Each positive biological sample can be taken from the biological sample grown in the eugonic medium, contained in the respective recipient 15 of the first analysis zone 14a.

In particular, in this second sampling and dispensing sub-step 64, which is preparatory to the execution of the antibiogram, in each of the first recipients 15a, also called reference sample, the positive biological sample from the culture medium is dispensed (positive flacon 15) already taken at the 0.5 McFarland turbidity level, while inside each of the second recipients 15b a specific antibiotic is also dispensed, in liquid form.

The control unit 18 selects each of the antibiotics on the basis of the type of bacteria identified and classified during the detection and classification sub-step 63.

Each of the antibiotics is present in liquid or lyophile form and is ready for dispensing, or is prepared at the moment so as to be optimized in the final concentration used.

After the second sampling and dispensing sub-step 64, there follows an antibiogram sub-step 65, during which the control unit 18, by means of the first examining devices 40, analyses the growth curves of the bacteria, both of the reference sample in the recipients 15a and also of the biological samples contained in the recipients 15b treated with different antibiotics.

The reference sample in the recipient 15a, without antibiotic, allows to calculate the percentage yield of the antibiotic (PGI, percentage growth inhibition) on the basis of the measurements carried out on the recipients 15b.

In particular the control unit 18 compares the growth curves of the reference sample with the growth or inhibition curves of the biological samples treated with different antibiotics, to verify the effectiveness of the antibiotic.

The analysis of the growth curves, and the possible inhibitions, determines the effectiveness of the antibiotic in vitro, by means of the categories, resistant (R), sensitive (S) or intermediate (I), which respectively indicate how much the bacterium resists the antibiotic and how much it is sensitive to it, in a similar way to the inhibition rings of the Kirby-Bauer method. A flat growth curve is equal to the "sensitive" classification, an exponential growth curve is equal to the "resistant" classification.

The curves can be shown graphically, and printed by the output device 19 (report following sub-step 65), and express the percentage of efficiency of the treatment for each antibiotic tested, as required for each clinical type or request for verification.

The percentage of effectiveness of the antibiotic in relation to the specific biological sample is expressed in percentage form from 0% (R=resistant bacterium) to 100% (S=sensitive bacterium) with respect to the reference biological sample, to which, as said, no antibiotic has been added.

With the invention, therefore, one can have an analysis of the yield or functionality of the antibiotics by means of the calculation of percentages of growth inhibition (PGI) by the bacteria, able to estimate the bactericide function of one or more antibiotics tested at the same time as the analysis. This calculation of percentages is advantageously carried out automatically, by means of an automatic comparison with the sample without the addition of an antibiotic.

There follows a description of a further working variant of the invention, in which the control unit 18 determines the number of units forming colonies per millimeter (in cfu/ml) for each specific positive biological sample, and on the basis of predefined data, associates this cfu/ml value to an appropriate quantity of antibiotic to be dispensed, correlated to the bacterial load.

In this way, the function of an antibiotic is correlated to the quantity of bacteria present in the biological sample. This information can be of interest in the studies of pharmacokinetics.

According to a further variant, in order to comply with the best choice of antibiotic with respect to the type of bacteria, a verification sub-step 65b with rotating sensor is provided, carried out after the detection and classification sub-step 63 and before the second sampling and dispensing sub-step 64.

The verification sub-step 65b on each positive biological sample consists in the identification carried out as described as follows.

The control unit 18 carries out, on positive samples only, an analysis of the samples themselves no longer by means of the first examining device 40, but by means of the second examining device 49, obtaining a reading on the whole angle of 180°. This broad reading allows to detect all the variables of the laser diffusion, allowing to construct growth curves with characteristics which are easily identifiable for each type of bacteria.

The first container 12 can have a cylindrical shape, or similar shape, and have seatings for the corresponding test tubes 13 on lateral surfaces.

It may also be provided that the integral device 10, by means of the control unit 18, can verify the residual antibiotic power (RAP) in a determinate biological sample, with the purpose of ascertaining whether the patient to which the determinate biological sample refers is taking antibiotics or not.

According to another variant, the second examining device 49 can be disposed in correspondence with the first analysis zone 14a, to verify the presence and to identify the type of bacteria.

It can also be provided to dispose, in each seating 17a, 17b, a reading device 38 (FIG. 2), for example a bar code reader or a RFID tag reader, controlled by the control unit 18. The reading device 38 can read the information, for example from a bar code printed on a label, on every recipient 15, 15a, 15b, so as to univocally identify the recipient 15, 15a, 15b, the biological sample contained in it and consequently the patient from whom the biological sample has been taken.

It is also provided that the control unit 18 can memorize the movements, the sample takings and the dispensing carried out by the movement and selection unit 20. In this way the contents of any recipient 15, 15a, 15b can always be correlated to the respective patient.

According to the variant shown in FIGS. 7 and 8, as an alternative to the containers 15, 15a, 15b shown in FIGS. 1, 1a, 1b and 4 for the quick bacterial growth and for the antibiogram, one or more plates, or micro-plates 66 are used, of the standardized type, each comprising a plurality of wells, or micro-wells 67, advantageously heated, which act as containers for the quick bacterial growth and for the biochemical reactions described above.

Therefore, the plates or micro-plates 66 with wells or micro-wells 67 can advantageously substitute the recipients or phials 15 for cultural growth in a eugonic medium. For the first step A of bacterial growth, thermostated micro-plates 66 will be used. On the other hand, as far as the antibiogram step 65 of the third examining step C is concerned, the micro-plates 66 will be used, providing for each patient a well 67a for the reference growth in a plate 66a and wells 67b for the growth of the antibiotics (one for each drug analyzed) in one or more plates 66b (FIG. 1b). All the micro-plates 66, 66a, 66b are heated. Moreover, all the micro-plates 66, 66a, 66b of the standardized type comprise 96 or 384 wells 67, 67a, 67b and using them allows to drastically reduce the overall bulk of the device with respect to a similar one which uses cylindrical recipients 15.

Using the plates 66, 66a, 66b, of limited dimensions, not only gives the advantage of producing a minor quantity of material which is potentially infected, but also allows to carry out biochemical reactions to identify the bacterial species.

For this purpose, in the first step A, one of the wells 67 is inoculated with the biological sample taken from the test tubes 13 and with the eugonic culture medium to carry out the bacterial growth test.

On the samples which are found positive, the reading of the 0.5 McFarland turbidity is carried out at the same time, calculated on the basis of the growth dynamics detected, and the antibiogram process is automatically activated.

It is also possible to use, in the appropriate instrument, a control latex with standard turbidity, so as to further control the 0.5 McFarland turbidity, by comparing it with a standardized latex at the desired level of turbidity, and the antibiogram process is automatically activated.

A third fraction of the sample is also taken from the well 67 (positive to growth), a part of this is inoculated into a new well 67a for the reference culture and another part of the third fraction is inoculated into others well 67b into which a suitable concentration of a specific antibiotic is added, in order to select the most suitable one (antibiogram).

Subsequently, in all wells (67a, 67b) dedicated to the antibiogram test (the first for the reference culture and the others for the culture with specific antibiotics) a eugonic growth medium will be added.

The high number of wells available also allows to fill others completely automatically with the same suspension obtained from the sample positive to bacterial growth in which, in each well 67, a different chemical reagent will be put. The different chemical reagents will cause, in the series of wells 67, a different combination of colors connected to a particular bacterial species.

The colorimetric reactions obtained in each well 67 can be evaluated, within a few hours, by means of a reading module 75 provided with a light source 68 which is faced by a photometer 69 on the opposite side of the plate 66 with the wells 67. This photometric reading system in micro-plate is used for possible bacterial identification.

To detect the combination of colors, the reading module 75 can also provide a sensor comprising a light source 70 disposed facing, on the opposite side of the plate 66, a CCD television camera 71 or other suitable sensor. The data detected can then be transmitted to the control unit 18 which, by means of suitable algorithms, discriminates the bacterial species on the basis of the resulting color combination.

A variant embodiment shown in FIG. 8 provides that the turbidity detection system comprises a laser emitter 41a positioned above the micro-plate 66 in correspondence with the wells 67 (this applies both for the micro-plates 66a used for bacterial growth and also for the micro-plates 66b used in the antibiogram as an alternative to the recipients 15a, 15b), and sensors 42a and 43a disposed respectively at 90° and 150° with respect to the lying plane P of the plate 66, positioned under the wells 67. This allows to apply a light scattering reading system to micro-plates, for application to culture tests, Raa tests (residual antibiotic activity) and antibiogram.

The invention claimed is:

1. An integrated device for diagnostic analyses used to verify the presence of bacteria in at least a biological sample mixed with a eugonic culture medium in a liquid form, to classify at least the type of bacteria, and to test a series of antibiotics selected from a group of characteristic antibiotics at least for said type of bacteria identified, thereby identifying those that are effective for an antibiotic therapy, the integrated device comprising, inside an integrated structure:

a first container that is provided with containing elements in which the biological samples to be analyzed are distributed;

a second container comprising at least one of a plurality of recipients and a plurality of micro-plates thermostated with wells, wherein some of the recipients or the micro-plates contain a eugonic culture medium in a liquid form in which a first fraction of the biological samples to be analyzed is dispensed, the plurality of recipients include a first recipient and a second recipient, and the plurality of micro-plates include a first micro-plate and a second micro-plate, the first and second micro-plates include a first well and a second well, respectively, wherein a further fraction of the biological samples which resulted positive to the analysis is dispensed in at least one of a pair of the first and second recipients and a pair the first and second wells;

a first examining device that is configured to verify the presence of bacteria in said biological samples contained in said first container and dispensed in the recipients and/or the micro-plates with wells to detect corresponding positive biological samples and to classify and/or identify at least a type of bacteria present in said positive biological samples in order to select a group of antibiotics appropriate for treating the classified or identified type of bacteria;

a second examining device that is configured to verify, on at least one of said first recipient and said first well and on at least one of said second recipient and said second well, a sensitivity and/or a resistance of each positive biological sample to a series of antibiotics of the group of antibiotics selected by said first examining device;

a third container comprising plates containing a solid culture ground in which a second fraction of the biological sample corresponding to a sample found positive by said first examining device is sown in order to isolate and/or identify said bacteria;

a movement and selection unit governed by a control unit to automatically perform at least taking of the positive biological samples and distribution of the positive biological samples in said second container and in said third container;

wherein said first examining device comprises a reading system that is configured to detect an attainment of a given turbidity value of a bacterial suspension present in at least one of said recipients and micro-plates with wells obtained during an exponential bacterial growth step, the given turbidity value being 0.5 on the McFarland scale; and a fourth container in which at least a part of the primary biological sample contained in said first container is deposited using the movement and selection unit, wherein the fourth container comprises one or more refrigerated plates having wells, in which part of the primary biological sample is preserved;

wherein the integrated device is configured to use a calibrated loop-shaped tube to take from the fourth container and sow on Petri dishes, native or primary biological samples found to be positive to a culture test in a liquid culture ground in the second container, and the integrated device is configured to assess the correctness of the examination carried out by the first examination device.

2. The integrated device as in claim 1, wherein said second container has a first analysis zone in which the at least one of the recipients and the micro-plates with wells are provided, and a second analysis zone for at least one of said first recipient and said first well and at least one of said second recipient and said second well, said first examining device being associated at least with said first analysis zone and said second examining device being associated with said second analysis zone.

3. The integrated device as in claim 2, wherein said third container defines a culture zone on solid culture ground which provides first Petri dishes that are kept refrigerated and second Petri dishes that are thermostated after they have been sown.

4. The integrated device as in claim 2, wherein said movement and selection unit includes a device that is configured to take and deposit a desired quantity of each biological sample resulting positive to the culture in the at least one of the recipients and the micro-plates with wells directly from a corresponding recipient or well in order to mix it said quantity inside the second recipient or second well of the second analysis zone with at least one or more antibiotics of the series of antibiotics and a liquid culture, with the purpose of verifying the sensitivity or the resistance of the bacterium to said one or more antibiotics with respect to a desired quantity of said positive sample, or a reference sample, in the first recipient or the first well of the second analysis zone which, in order to define a reference of absolute growth, is mixed with the liquid culture without any antibiotic.

5. The integrated device as in claim 1, wherein the containing elements of said first container comprise a plurality of test tubes inside which a pure biological sample is present and said containing elements are also provided with a cooling system associated with said containing elements in order to guarantee a correct conservation of the samples.

6. The integrated device as in claim 1, wherein said second container comprises a heating unit that is configured to heat said biological samples in order to promote bacterial growth.

7. The integrated device as in claim 2, further comprising a selection system that is configured to take a desired quantity of a pure biological sample contained in a test tube in order to dispense said quantity in a specific recipient and/or well containing a eugonic medium and disposed in said first analysis zone associated with said first examining device.

8. The integrated device as in claim 7, wherein said selection system is further configured to take a desired quantity of a positive biological sample enriched and contained in a recipient or well, disposed in said first analysis zone, so as to divide said quantity into a plurality of a pair of first and second recipients and/or a pair of first and second wells disposed in said second analysis zone.

9. The integrated device as in claim 2, wherein the recipients of the second analysis zone are divided into first recipients and second recipients, wherein inside each of said second recipients, an antibiotic of a group of antibiotics suitable for the type of bacteria identified by said first examining device is introduced, together with the positive biological sample and the liquid culture, and wherein inside each of said first recipients, the positive biological sample of reference is present exclusively with the liquid culture, without any antibiotic.

10. The integrated device as in claim 9, wherein said second examining device is configured to compare the development of the bacterial load of the biological samples contained in each of the second recipients with the development of the bacterial load of the corresponding determinate positive biological sample contained in at least one of the first recipients which functions as a reference.

11. The integrated device as in claim 1, wherein each of said first and second examining devices comprises an emitter of electromagnetic radiation, and a detector of said electromagnetic radiation which passes through said recipient or well.

12. The integrated device as in claim 11, wherein the detector of said first examining device has at least two fixed sensor elements, and wherein the detector of said second examining device has at least a movable sensor element.

13. The integrated device as in claim 12, wherein the detector of the first and the second examining devices has at least a movable sensor element.

14. The integrated device as in claim 13, wherein said fixed sensor elements are disposed respectively at about 90° and 150° with respect to said emitter and along a circumference at the center of which said recipient is disposed.

15. The integrated device as in claim 13, wherein said fixed sensor elements are disposed respectively at about 90° and 150° with respect to the plane on which the plate lies.

16. The integrated device as in claim 1, wherein the third container is provided in order to evaluate the correctness of the examination carried out by the first examining device and/or the second examining device.

17. The integrated device as in claim 1, wherein said movement and selection unit comprises a movement mechanisms of at least a sampling and dispensing needle.

18. The integrated device as in claim 17, further comprising, in said integrated structure, a device to wash and sterilize said sampling and dispensing needle.

19. The integrated device as in claim 1, wherein the control unit is configured to at least memorize the movements, the samplings and the dispensations carried out by said selection means.

20. The integrated device as in claim 1, comprising, in the first analysis zone, one or more micro-plates defining a plurality of wells, each of which is able to be filled with the biological sample taken from the test tubes and with a eugonic medium in order to carry out the culture test, in which, in the second analysis zone, exclusively for the samples positive to the culture test, a first well of a plate being configured to be filled with a bacterial suspension obtained from the positive sample previously regulated at 0.5 McFarland, and with a eugonic medium to obtain a reference growth sample, wherein one or more wells of a plate is configured to be filled with the same bacterial suspension and the same eugonic medium with the addition of an antibiotic in order to select the antibiotic most suitable for the specific bacterium.

21. The integrated device as in claim 20, comprising a sensor for detecting turbidity and/or detecting a growth or an inhibition kinetics in each of said wells which contain the bacterial suspension and a relative antibiotic.

22. The integrated device as in claim 20, wherein in at least some of said wells, a chemical reagent is added to the bacterial suspension, the device comprising a sensor for detecting the color combination produced by said chemical reagents in order to identify the bacterial type on the basis of the resulting color combination.

23. A method of using the integrated device according to claim 1 for diagnostic analyses used to verify the presence of bacteria in at least a biological sample mixed with a liquid culture ground, or eugonic medium, in order to identify at least the type of bacteria, and to test a series of antibiotics, selected from a group of antibiotics characteristic at least for said type of bacteria identified, identifying those effective to determine the antibiotic therapy or to monitor the effectiveness of the antibiotic administered to the patient, the method comprising the following steps:
  a first examining step, during which a first fraction of the content of a plurality of primary biological samples is examined so as to verify the presence of bacteria in order to define a plurality of positive biological samples, and to identify or classify at least the type of bacteria so as to define said group of antibiotics;
  a second examining step in which a second fraction of the biological sample corresponding to a sample found positive is inoculated or sown in a solid culture ground in order to obtain the isolation and/or identification of said bacteria; and
  a third examining step, during which the sensitive or resistant response of each positive biological sample to a series of antibiotics of said group of antibiotics defined in said first examining step is verified on the enriched positive sample after the culture test, wherein a reading operation is carried out to detect the attainment of a given level of turbidity equal to 0.5 on the McFarland scale of the bacterial suspension obtained during the exponential bacterial growth step,
  wherein the second examining step also provides a dispensation sub-step of each of the primary biological samples, or a fraction of each of the primary biological samples, in a fourth container, which function as a storage zone, and
  the second examining step provides a dispensation and culture sub-step in which a second fraction of each biological sample previously found positive and preserved in the fourth storage container, corresponding to a sample found positive, is inoculated or sown in a third container provided with Petri dishes having a solid culture ground, in order to obtain confirmation of the fast growth data, by isolating the colonies and by subsequently identifying the bacterial types.

24. The method as in claim 23, wherein the third examining step uses the liquid culture ground or eugonic medium of the sample positive to the bacterial growth of the first examining step.

25. The method as in claim 23, providing a sub-step of taking the primary sample from a test tube, a sub-step of dispensing or sowing a part of the primary sample inside recipients or plates with wells and a detection and classification sub-step to verify the presence of pathogenic organisms and the kinetic reading of the recipients or wells, at periodic intervals by examining devices in order to detect the samples positive to bacterial growth and possibly to identify or classify the bacterium in order to define the group of antibiotics suitable for said bacterium.

26. The method as in claim 25, wherein in the first sampling sub-step a desired quantity of a pure biological sample contained in a respective test tube disposed in a first container is selected and taken, and in the second dispensation sub-step, said desired quantity is dispensed in a recipient or plate with wells, disposed in a second container, and containing the liquid culture ground or eugonic medium, in order to promote the bacterial growth.

27. The method as in claim 23, providing to examine the isolations obtained in the Petri dishes and possibly to modify the results of the clinical antibiogram.

28. The method as in claim 23, wherein during said third examining step each positive biological sample is mixed with at least one antibiotic of said series of antibiotics, in order to verify the sensitivity or the resistance of the bacterium to said antibiotic with respect to a positive reference sample, to which no antibiotic has been mixed.

29. The method as in claim 23, wherein the third examining step provides a sampling and dispensation sub-step in which, after the turbidity level has reached 0.5 McFarland in the recipients or wells of the biological samples positive to the culture test, a volume of said culture medium is inoculated in a clinical antibiogram panel, consisting of a first recipient or first well for reference growth and second recipients or second wells containing specific antibiotics in order to verify, in an antibiogram sub-step, the sensitivity or resistance of the bacterium to said antibiotic with respect to a reference sample to which no antibiotic has been mixed.

30. The method as in claim 29, wherein in the sampling and dispensation sub-step, carried out after said first examining step, a desired quantity of a specific positive biological sample enriched with the presence of grown bacteria is taken, in order to divide said quantity in a plurality of second recipients or second wells inside each of which an antibiotic of said group of characteristic antibiotics at least for said types of bacteria is present.

31. The method as in claim 29, wherein in the antibiogram sub-step of the third examining step, having read said clinical antibiogram panel, the sensitive, intermediate, resistant response of each positive biological sample to a series of antibiotics is verified.

32. The method as in claim 23, wherein the third examining step also comprises a verification sub-step in which the control unit carries out an analysis, on only the positive samples, by a second examining device, obtaining a reading over the whole angle of 180°, in order to allow the construction of growth curves with identifiable characteristics for every type of bacteria.

\* \* \* \* \*